(12) United States Patent
Barnes et al.

(10) Patent No.: US 9,849,093 B2
(45) Date of Patent: Dec. 26, 2017

(54) COMPOSITIONS AND METHODS FOR ADMINISTRATION TO SUBJECTS WITH DYSPHAGIA

(71) Applicant: Cape Spear Pharmaceuticals, Ltd., Ottawa (CA)

(72) Inventors: David Barnes, Ottawa (CA); Jonathan Barker, Ottawa (CA); Stephen Haggerty, Paradise (CA)

(73) Assignee: Cape Spear Pharmaceuticals, Ltd., Ottawa (CA)

( * ) Notice: Subject to any disclaimer, the term of this patent is extended or adjusted under 35 U.S.C. 154(b) by 0 days.

(21) Appl. No.: 14/421,940

(22) PCT Filed: Mar. 14, 2014

(86) PCT No.: PCT/IB2014/001041
§ 371 (c)(1),
(2) Date: Feb. 16, 2015

(87) PCT Pub. No.: WO2014/140867
PCT Pub. Date: Sep. 18, 2014

(65) Prior Publication Data
US 2016/0213622 A1   Jul. 28, 2016

Related U.S. Application Data

(60) Provisional application No. 61/788,038, filed on Mar. 15, 2013.

(51) Int. Cl.
| *A61K 9/14* | (2006.01) |
| *A61K 9/50* | (2006.01) |
| *A61K 31/138* | (2006.01) |
| *A61K 31/4425* | (2006.01) |
| *A61K 31/34* | (2006.01) |

(52) U.S. Cl.
CPC .......... *A61K 9/5073* (2013.01); *A61K 9/5047* (2013.01); *A61K 31/138* (2013.01); *A61K 31/34* (2013.01); *A61K 31/4425* (2013.01)

(58) Field of Classification Search
None
See application file for complete search history.

(56) References Cited

U.S. PATENT DOCUMENTS

| 5,270,056 | A | 12/1993 | Berglund | |
| 2002/0031796 | A1* | 3/2002 | Townsend | C12Q 1/04 435/34 |
| 2002/0034475 | A1* | 3/2002 | Ribi | A23L 1/275 424/9.6 |
| 2004/0228802 | A1 | 11/2004 | Chang et al. | |
| 2011/0129591 | A1* | 6/2011 | Jordan | A23L 2/52 426/599 |
| 2012/0189703 | A1 | 7/2012 | Fallon et al. | |
| 2014/0127307 | A1 | 5/2014 | Venkatesh et al. | |

FOREIGN PATENT DOCUMENTS

| EP | 1809251 B1 | 7/2007 |
| WO | 2012145446 A1 | 10/2012 |

OTHER PUBLICATIONS

Genton P. "Progress in pharmaceutical development presentation with improved pharmacokinetics: a new formulation for valproate", Acta Neurolog. Scand., 2005: 112 (Suppl. 182): pp. 26-32.
International Search Report and Written Opinion of related International Application No. PCT/IB2014/001041, filed Mar. 14, 2014, mailed Oct. 24, 2014.

\* cited by examiner

*Primary Examiner* — Robert T Crow
*Assistant Examiner* — John P Nguyen
(74) *Attorney, Agent, or Firm* — Lathrop Gage LLP

(57) ABSTRACT

Provided are novel methods and compositions for administration of pharmaceuticals to subjects with dysphagia. Pharmaceuticals are associated with beads and administered with food, beverage or cosmetic to provide ease of administration to subjects with dysphagia. Environmental indicators are associated with beads for Quality Assurance.

19 Claims, No Drawings

COMPOSITIONS AND METHODS FOR ADMINISTRATION TO SUBJECTS WITH DYSPHAGIA

RELATED APPLICATION

This application is a 35 U.S.C. 371 of PCT/IB2014/001041, filed Mar. 14, 2014, which claims priority from U.S. Provisional Patent Application No. 61/788,038, filed on Mar. 15, 2013. The entire contents of these applications are incorporated by reference, herein, in their entirety.

BACKGROUND OF THE INVENTION

Drug administration in people with swallowing difficulties (dysphagia), particularly the elderly, is challenging. For example, residents in extended care facilities take an average of nine medications daily, ranging from vitamins to support an anti-osteoporosis regimen, through to cardio-vascular medications of varying types—blood pressure, cholesterol lowering, diabetes medications and so on. Typical drug administration is three or even four times a day. Thirty-five percent of patients in these facilities have difficulty swallowing.

Solid oral dosage forms (e.g. pills or tablets etc.) come in a variety of size, shapes, textures and coatings and are generally unpleasant and time consuming to administer, even for people who can manage to swallow them, due to size, stickiness, taste, aftertaste or frequency of administration. In people who have dysphagia, swallowing solid oral dosage forms may be very painful, if not impossible (e.g. stroke patients).

A standard method of drug administering solid oral medications such as tablets and pills is to grind them using a crushing device (manual or motorized) and mix them with whatever food the patient will tolerate. This process disrupts the fundamental behavior of the medicine. For the patient, it can result in toxicity if the drug is absorbed quicker than usual or if the blood concentration becomes too high (dose dumping). The drug effects (desirable clinical effects) may wear off quicker than usual, leaving the patient 'unmedicated' until the next dose. It also results in unpleasant experiences for patients due to bad taste or unpleasant texture making administration even more challenging for staff. Crushing pills can result in dosing inaccuracy as powdered drug can be left behind in the crushing device or lost during transfer to the food. The process of crushing can aerosolize the drug and it can be inhaled by staff or patients, a clear safety issue. Crushing pills by staff can result in repetitive strain or other workplace injury, a significant logistical and economic problem for facilities. In addition, among many other problems, grinding and mixing medications results in exposure of the active pharmaceutical ingredient (API) to an environment it was not designed or approved for, in terms of acidity, temperature, liquid exposure, dissolution outside of the patient's own body, and other factors. Compounding this problem, long acting formulations of some drugs have been developed to reduce the frequency of administration to once daily from 2-4 times daily; these long acting pills that cannot be ground up because to do so would release a potentially dangerous bolus of medications to the patient. Yet this is consistently the primary method by which drugs are administered to these challenging patients.

There is a need in the art for pharmaceutical compositions that are easily taken by subjects with difficulty swallowing and methods of making and administering these compounds.

SUMMARY

The disclosure provides a composition comprising an active pharmaceutical ingredient, a bead and an indicator. In one embodiment, the composition is formulated to alleviate difficulty swallowing in a subject in need thereof. The subject in need thereof can be suffering from dysphagia. In certain embodiments, the composition is formulated to be safe and efficacious when administered to the subject in food, beverage or cosmetic. In other embodiments the compositions are designed for compatibility with and stability in foodstuffs. The mouthfeel, taste, smell and/or texture of the food, beverage or cosmetic is generally not substantially changed from food, beverage or cosmetic not comprising the composition in the subject in need thereof.

In some embodiments, the indicator provides information regarding pH, the presence of temperature changes and the occurrence of freeze-thaw. According to some aspects of this embodiment, the indicator provides information regarding lowering of pH below about 8.0, 7.5, 7.0 or 6.5 or 6.0 or 5.5 or 5.0 or 4.5 or 4.0 In other aspects of this embodiment, the indicator provides information regarding raising of pH above 4.0 or 4.5 or 5.0 or 5.5 or 6.5 or 6.5 or 7.5 or 8.0.

In other embodiments, composition of the beads that contain active pharmaceutical ingredient allows for visual identification by color of the beads when mixed with food or other administration matrices or crushed solid oral drug products. The composition of the beads that contain active pharmaceutical ingredient can also show when bead integrity is compromised due to solubilization.

In another embodiment, the indicator provides information regarding a temperature change wherein the temperature drops below 10 or 5° C. In yet another embodiment, the indicator provides information regarding a temperature change wherein the temperature rises above 30 or 50° C.

In certain embodiments, the indicator changes color in order to provide information. The color change can be from white or gray to red, green, blue, orange, yellow or violet. In other more specific embodiments, the indicator is selected from the group consisting of: a dark blue and light blue indicator once sold under the trademark REFLEX BLUE™, Black Pantone 7C 2x, Red 192, Process Magenta, Orange 165, Green 349, green C, Purple 2735, Yellow 100U, gentian violet, leucomalachite green, thymol blue, methyl yellow, bromophenol blue, congo red, methyl orange, screened methyl orange, bromocresol green, methyl red, azolitmin, bromocresol purple, bromothymol blue, phenol red, a eurhodin dye once sold under the trademark NEUTRAL RED™, naphtholphthalein, cresol red, phenolphthalein, thymolphthalein and alizarene yellow R.

In other embodiments the indicator may be comprised of a colored layer that is exposed when an outer layer or layers is changed by the environmental conditions. In one embodiment the bead is coated with a polymeric chemical that degrades above a certain temperature, exposing a colored indicator layer underneath. In another embodiment, the bead is coated with a polymeric chemical that fractures at or below 0 degrees Celsius revealing a colored indicator layer underneath. In another embodiment the bead is coated with a polymeric chemical that will degrade when exposed to low pH, revealing a colored indicator layer underneath. In another embodiment the bead is coated with a polymeric chemical that will degrade when exposed to high pH, revealing a colored indicator layer underneath. In another embodiment, the beads are between 50 and 200, 50 and 100, 50 and 1000 and 50 and 300 μm in diameter.

In other embodiments, the composition comprises two groups of beads, wherein the first group of beads comprises the active pharmaceutical ingredient and the second group comprises the indicator. The beads of the first group can be between 50 and 200, 50 and 100, 50 and 1000 and 50 and 300 μM in diameter. The beads of the second group can be between 50 and 1000, 50 and 750, 50 and 750 and 50 and 200 μm in diameter.

In another embodiment the indicator beads population may be comprised of one population of beads that indicate all environmental parameters described, being pH, freeze/thaw, and high temperature. In other embodiments the indicator beads population may be comprised or two or three or more bead sub-populations each of which indicates one single environmental parameter. In one embodiment the population of indicator beads would be comprised of three distinct populations of indicator beads, one of which would indicate temperature excursion, the second of which would indicate pH excursion, the third of which would indicate freeze/thaw.

In one embodiment the indicator bead population is packaged separately from the medicinal beads population. In another embodiment indicator beads for each environmental parameter are packaged separately.

In another embodiment, the active pharmaceutical ingredient is selected from the group consisting of Nifedipine, Metoprolol succinate, isosorbide mononitrate, furosemide, hydrochlorothiazide, diltiazem, verapamil, digoxin, enalapril, lisinopril, ramipril, amlodipine, theophylline, ferrous fumarate and gluconate, atorvastatin, rosuvastatin, levothyroxine, metformin, potassium chloride, trazodone, carbidopa/levodopa, gabapentin, carbamazepine, bupropion, olanzapine, chlorpromazine, valproic acid, clarithromycin, azithromycin, ciprofloxacin, amoxicillin, naproxen sodium, prednisone, acetaminophen, ibuprofen and ranitidine.

The disclosure also provides a method of making a dosage form comprising adding the composition to a food, beverage or cosmetic.

The disclosure also provides a kit including an active pharmaceutical ingredient and a first group of beads and an indicator and a second group of beads, wherein the active pharmaceutical ingredient and the first group of beads are provided in a first container and the indicator and the second group of beads are provided in a second container.

The disclosure also provides a kit wherein indicator beads for each individual environmental parameter are provided in individual containers. In another embodiment combinations of two or more indicators are provided in a container. In another embodiment, in additional individual containers wherein individual containers can contain: a single population of beads, wherein each bead contains a plurality of indicators, a single population of beads wherein each bead contains one individual indicator, a single population of beads wherein each bead contains combinations of two or more indicators, a mixed population of beads, wherein the container contains a mix of two or more beads and wherein each bead contains one individual indicator.

In one embodiment, the beads of the first group are between 50 and 200, 50 and 100, μM in diameter or have an average diameter between 50 and 200, 50 and 100. In another embodiment, the beads of the second group are between or have an average diameter between 50 and 1000, 50 and 750, 50 and 500 and 50 and 200 μm in diameter.

In another embodiment, the active pharmaceutical ingredient is selected from the group consisting of Nifedipine, Metoprolol succinate, isosorbide mononitrate, furosemide, hydrochlorothiazide, diltiazem, verapamil, digoxin, enalapril, lisinopril, ramipril, amlodipine, theophylline, ferrous fumarate and gluconate, atorvastatin, rosuvastatin, levothyroxine, metformin, potassium chloride, trazodone, carbidopa/levodopa, gabapentin, carbamazepine, bupropion, olanzapine, chlorpromazine, valproic acid, clarithromycin, azithromycin, ciprofloxacin, amoxicillin, naproxen sodium, prednisone, acetaminophen, ibuprofen and ranitidine.

In other embodiments, the indicator provides information regarding pH, the presence of temperature changes and the occurrence of freeze-thaw. According to some aspects of this embodiment, the indicator provides information regarding lowering of pH below about 8.0, 7.5, 7.0, 6.5, 6.0, 5.5 or 5.0. According to other aspects of this embodiment, the indicator provides information regarding raising of pH above about 5.0, 5.5, 6.0, 6.5, 7.0 7.5 or 8.0.

In another embodiment, the indicator provides information regarding a temperature change wherein the temperature drops below 10 or 5° C. In yet another embodiment, the indicator provides information regarding a temperature change wherein the temperature rises above 30 or 50° C.

In certain embodiments, the indicator changes color in order to provide information. The color change can be from white or gray to red, green, blue, orange, yellow or violet. In other more specific embodiments, the indicator is selected from the group consisting of: a dark blue and light blue indicator once sold under the trademark REFLEX BLUE™, Black Pantone 7C 2x, Red 192, Process Magenta, Orange 165, Green 349, green C, Purple 2735, Yellow 100U, gentian violet, leucomalachite green, thymol blue, methyl yellow, bromophenol blue, congo red, methyl orange, screened methyl orange, bromocresol green, methyl red, azolitmin, bromocresol purple, bromothymol blue, phenol red, a eurhodin dye once sold under the trademark NEUTRAL RED™, naphtholphthalein, cresol red, phenolphthalein, thymolphthalein and alizarene yellow R.

In some embodiments the indicator may be comprised of a colored layer that is exposed when an outer layer or layers is changed by the environmental conditions. In one embodiment the bead is coated with a polymeric chemical that degrades above a certain temperature, exposing a colored indicator layer underneath. In another embodiment, the bead is coated with a polymeric chemical that fractures at or below 0 degrees Celsius revealing a colored indicator layer underneath. In another embodiment the bead is coated with a polymeric chemical that will degrade when exposed to low pH, revealing a colored indicator layer underneath. In another embodiment the bead is coated with a polymeric chemical that will degrade when exposed to high pH, revealing a colored indicator layer underneath.

The disclosure also provides a method of administering an active pharmaceutical ingredient to a subject with difficulty swallowing comprising formulating the active pharmaceutical ingredient, thereby alleviating difficulty swallowing the active pharmaceutical ingredient in the subject with difficulty swallowing. In one embodiment, the subject in need thereof suffers from dysphagia. In another embodiment, the composition, that is designed and formulated specifically for compatibility, safety and efficacy when mixed with food, is administered to the subject in food, beverage or cosmetic.

In other embodiments, the method also includes sprinkling the formulated active pharmaceutical ingredient that is designed for administration in food, into or onto the food, beverage or cosmetic. In additional embodiments, the method also includes mixing the formulated active pharmaceutical ingredient that is designed for administration in food, into or onto the food, beverage or cosmetic.

According to some embodiments, the mouthfeel, taste, smell or texture of the food, beverage and/or cosmetic is not substantially changed from food, beverage or cosmetic not sprinkled or mixed with the formulated active pharmaceutical ingredient.

In certain embodiments, the microformulating step comprises coating beads with the active pharmaceutical ingredient. In other embodiments, the beads are between 50 and 200 or 50 and 100 μM in diameter or have an average diameter between 50 and 200 or 50 and 100 μm.

In other embodiments, the method also includes adding an indicator to the formulated active pharmaceutical ingredient. In certain embodiments, the indicator provides information regarding pH, temperature changes and the occurrence of freeze-thaw. According to some aspects of this embodiment, the indicator provides information regarding lowering of pH below about 8.0, 7.5, 7.0, 6.5, 6.0, 5.5 or 5.0. According to other aspects of this embodiment, the indicator provides information regarding raising of pH above about 5.0, 5.5, 6.0, 6.5, 7.0 7.5 or 8.0.

In another embodiment, the indicator provides information regarding a temperature change wherein the temperature drops below 10 or 5° C. In yet another embodiment, the indicator provides information regarding a temperature change wherein the temperature rises above 30 or 50° C.

In certain embodiments, the indicator changes color in order to provide information. The color change can be from white or gray to red, green, blue, orange, yellow or violet. In other more specific embodiments, the indicator is selected from the group consisting of: a dark blue and light blue indicator once sold under the trademark REFLEX BLUE™, Black Pantone 7C 2x, Red 192, Process Magenta, Orange 165, Green 349, green C, Purple 2735, Yellow 100U, gentian violet, leucomalachite green, thymol blue, methyl yellow, bromophenol blue, congo red, methyl orange, screened methyl orange, bromocresol green, methyl red, azolitmin, bromocresol purple, bromothymol blue, phenol red, a eurhodin dye once sold under the trademark NEUTRAL RED™, naphtholphthalein, cresol red, phenolphthalein, thymolphthalein and alizarene yellow R.

In some embodiments the indicator may be comprised of a colored layer that is exposed when an outer layer or layers is changed by the environmental conditions. In one embodiment the bead is coated with a polymeric chemical that degrades above a certain temperature, exposing a colored indicator layer underneath. In another embodiment, the bead is coated with a polymeric chemical that fractures at or below 0 degrees Celsius revealing a colored indicator layer underneath. In another embodiment the bead is coated with a polymeric chemical that will degrade when exposed to low pH, revealing a colored indicator layer underneath. In another embodiment the bead is coated with a polymeric chemical that will degrade when exposed to high pH, revealing a colored indicator layer underneath.

According to some embodiments, the active pharmaceutical ingredient coats a first group of beads and the indicator coats a second group of beads. In another embodiment, the subject is a mammal. In some aspects of the embodiment, the subject is a human. In other aspects of this embodiment, the human is greater than 65 years in age.

DETAILED DESCRIPTION

The disclosure provides pharmaceutical compositions that are easier to swallow than solid oral dosage forms. In certain embodiments, the pharmaceuticals described herein can be administered less frequently than solid oral dosage forms.

According to further embodiments, the pharmaceutical compositions described herein also include an "indicator" capability that warns of certain potential issues relating to product identity, integrity, food compatibility and medication co-administration compatibility. In certain embodiments, indicators provide signals showing the identity of an API associated with the indicator. In other embodiments, indicators can also change in signal when changes in the API integrity, compatibility of the API with food or other medications that are co-administered with the API occur. In certain embodiments, more than one type of indicator is used. In certain specific embodiments, indicators that show identity of an API are used with indicators that show changes in status of the integrity, food compatibility and medication co-administration compatibility of the API.

In certain embodiments, the pharmaceutical compositions described herein is a powder, coated bead or granular technology, which offers the greatest flexibility in terms of drugs that can be incorporated while meeting the specific administration to subjects with dysphagia. These compositions can be combined with various types of food, beverage and/or cosmetics to aid in administration of APIs to subjects with dysphagia. Particularly, the pharmaceuticals can be combined with various types of food or beverage. In other embodiments, the pharmaceuticals can be combined with various types of food.

I. Dysphagia

Subjects with dysphagia have difficulty swallowing. Subjects with dysphagia can have oropharyngeal dysphagia, esophageal dysphagia or functional dysphagia. Oropharyngeal dysphagia can arise from abnormalities of muscles, nerves or structures of the oral cavity, pharynx, and upper esophageal sphincter. Esophageal dysphagia can arise from the body of the esophagus, lower esophageal sphincter, or cardia of the stomach, usually due to mechanical causes or motility problems. Functional dysphagia is when a subject has trouble swallowing but no organic cause of the dysphagia can be found. Functional dysphagia is more common in the geriatric population because the ability to swallow usually deteriorates with old age. The compositions and methods described herein can be used to administer active pharmaceutical ingredients (API; drug substance; medicine) to subjects with any form of dysphagia.

Symptoms of dysphagia include difficulty controlling food in the mouth, inability to control food or saliva in the mouth, difficulty initiating a swallow, coughing, choking, frequent pneumonia, unexplained weight loss, gurgly or wet voice after swallowing and nasal regurgitation. Dysphagia occurs more often in elderly subjects, subjects who have suffered strokes and subjects admitted to acute care hospitals or chronic care facilities. Other causes of dysphagia include head and neck cancer, progressive neurologic diseases such as Parkinson's disease, dementia, multiple sclerosis, multiple system atrophy, or amyotrophic lateral sclerosis. The compositions and methods described herein can be used to more easily administer API to subjects with any of the above pathologies or symptoms or to geriatric patients, mitigating the discomfort and pain associated with swallowing solid oral dosage forms (e.g. pills, tablets).

As used herein, "geriatric patients" refers to human subjects of greater than 50 years of age suffering from a pathology or dysfunction that requires help from a medical professional. According to other embodiments, geriatric patients are human subjects of greater than 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 years old. Geriatric patients can also refer to mammalian non-human subjects of advanced age that are suffering from a pathology that requires help from a veterinary professional. Geriatric patients that are mammalian non-human subjects have advanced through greater than 60% of the normal life expectancy for their species. In other embodiments, the mammalian non-human subjects have advanced through greater than 65, 70, 75, 80, 85, 90 or 95% of the normal life expectancy for their species.

II. Beads

In certain embodiments, the APIs administered according to this disclosure are associated with beads. The size of the beads allows the API to be administered with a food, beverage or cosmetic without changing the texture, smell and/or taste of the food, beverage or cosmetic.

Beads appropriate for use according to the compositions and methods described herein are smaller than 1000 µM in diameter. According to other embodiments, the beads appropriate for use according to the compositions and methods described herein are smaller than 1000, 950, 900, 850, 800, 750, 700, 650, 600, 550, 500, 450, 400, 350, 300, 290, 280, 270, 260, 250, 240, 230, 220, 210, 200, 190, 180, 170, 160, 150, 140, 130, 120, 110, 100, 90, 80, 70, 60, 50, 40, 30, 20 or 10 µm in diameter. According to other embodiments, the beads appropriate for use according to the compositions and methods described herein are between 50 and 300 µm in diameter.

In certain embodiments, beads appropriate for use according to the compositions and methods described herein are smaller than 300 µm in diameter. According to other embodiments, the beads appropriate for use according to the compositions and methods described herein are smaller than 290, 280, 270, 260, 250, 240, 230, 220, 210, 200, 190, 180, 170, 160, 150, 140, 130, 120, 110, 100, 90, 80, 70, 60, 50, 40, 30 20 or 10 µm in diameter. According to other embodiments, the beads appropriate for use according to the compositions and methods described herein are between 50 and 300 µm in diameter. Smaller beads are particularly useful for being associated with API Smaller beads have less of an effect on mouthfeel, texture and taste when the beads are mixed with food, beverage or cosmetics.

According to other embodiments, the beads appropriate for use according to the compositions and methods described herein are between 70 and 200 µM in diameter. According to other embodiments, the beads appropriate for use according to the compositions and methods described herein are between 10 and 50, 50 and 100, 100 and 150, 150 and 200, 200 and 250, 250 and 300, 50 and 250, 50 and 200, 50 and 150, 70 and 250, 70 and 150, 70 and 100 or 100 and 200 µM in diameter.

API can be associated with beads according to any method known in the art. The bead API compositions can be made on microparticles of the API, itself. In other embodiments, the API is associated with beads of various compositions.

The bead compositions described herein can be manufactured according to any method known in the art. Methods known in the art include extrusion and spheronization, drug layering, hot melt extrusion, mini-tabs, spray congealing, direct pelletization and high shear melt pelletization. In certain embodiments, the bead compositions described herein are manufactured by extrusion and spheronization or drug layering or hot melt extrusion or pelletization. Extrusion and spheronization involves a multi-step process including dry mixing, wet massing, extrusion, spheronization and drying steps. Wet massing uses high shear/planetary/Hobart/sigma blade mixer. Extrusion uses various screen sizes. Spheronization is accomplished with a marumizer with different sizes of cross hatch plates. Beads can be coated with various layers of coatings. Drug layering involves deposition of successive layers of drug from solution or suspension on substrates which may be crystals or granules of the same material or inert beads. Sugar spheres or MCC (non-pareil seeds) are the most common starting materials. Drug particles are dissolved/suspended in the binding liquid and sprayed on to the sugar spheres in a fluid bed coater equipped with Wurster column Hot melt extrusion involves solid dispersion of active pharmaceutical ingredients (APIs) in a polymeric matrix. The goal is to disperse drugs in a matrix at the molecular level to form solid solutions or dispersions. It is a single step continuous process that produces pellets/beads with solid solution/dispersion of API in excipients. Functional excipients can be matrix polymers such as PVP, PVP-VA, polyethylene co-vinyl acetate, polyethylene glycols, cellulose ethers and acrylates, polyethylene oxides, PLGA, low melting waxes, bees wax, carnauba wax, cetyl palmitate, gleceryl behanate, gleceryl monostearate, hydrogenated castor oil, stearic acid, stearic alcohol. Plasticizers can be used including but not limited to low molecular weight polyethylene glycols. Bulking agents and other ingredients such as colors and antioxidants can be included. Pelletization can include direct pelletization-rotogranulation, and high shear melt pelletization. Rotogranulation is where dry blended material containing API is wetted with solvent or binder system and subjected to centrifugal motion simultaneously producing agglomerates. High shear melt includes pelletization by heating and massing a dry powder mixture. API, binder and other excipients are mixed and heated to beyond the melting point of the binder. Binders can be stearic acid, glycerol monostearate, hydrated castor oil and polyethylene glycols or others.

III. Indicators

The compositions described herein can also include indicators. These indicators are used to monitor various parameters associated with API administration, particularly when the API is first mixed with or sprinkled on food, beverage or cosmetic. The parameters that can be monitored include pH, temperature and freeze/thaw. The indicators operate by creating a signal when a threshold for a parameter is reached. In certain embodiments, this signal is a color change. However, any signal method known in the art could be used. These methods include signals based on changes in fluorescence, magnetic properties, ionic properties, electrochemical properties or resonance properties. Indicators have a home configuration wherein a first signal is produced and at least a first threshold configuration wherein a second signal is produced. The indicator changes from a home to a first threshold configuration upon passing a threshold in a measured parameter. According to certain embodiments, the indicators used herein have more than one threshold. In certain embodiments, the indicators described herein have 2, 3, 4, 5, 6, 7, 8, 9, 10 or more threshold configurations that are reached through exposing the indicator to a given parameter as different ranges.

In one example, an indicator operates as follows. For the purposes of this example, an indicator detected pH changes. The indicator is in its home configuration when it is exposed to a pH between 6.5 and 7.5. At this pH range, the indicator is a neutral color. At a pH≤6.5 the indicator's first threshold is reached. In the first threshold configuration, the indicator changes color to red. At a pH>7.5 the indicator's second threshold is reached. In the second threshold configuration the indicator changes color to blue.

In certain embodiments, when a threshold is reached, the indicator retains the color associated with the configuration caused by passing that threshold, even if the conditions the indicator is exposed to change so that the indicator is no longer exposed to a value of a parameter that is beyond the threshold. For example, an indicator that has a first threshold of pH<6.0 is exposed to a pH of 5.5. The indicator attains its first threshold configuration and changes color, here to red. Later, the pH the indicator is exposed to increases to 7.3. In this example, the indicator would retain the color associated with its first threshold configuration. In other embodiments, the color of the indicator reflects the value of the parameter that it is presently exposed to. Thus, in this example, an indicator would change from the color associated with its first threshold and back to the color associated with its home configuration if conditions changed from those that trigger the first threshold configuration and then back to conditions that are associated with the home configuration.

The color used for each configuration can be any known in the art as long as the colors for the various configurations can be distinguished from each other. Colors that can be used include white, black, brown, grey, red, orange, yellow, green, blue or violet. However, any color across the visible spectrum could be used. Indicators that differentially reflect light outside the visible spectrum (e.g. ultraviolet and infrared) could also be used. In certain embodiments, the color used for the home configuration is neutral so that the indicator is not detectable to the naked eye when mixing the indicator with food, beverage or cosmetics. In these embodiments, the first and other threshold configurations are represented by colors that are detectable to the human eyes. In other embodiments, the indicator is detectable to the human eye in its home configuration as well as in threshold configurations. In other embodiments, the indicator is detectable in its home configuration but not in at least some threshold configurations.

According to certain embodiments, the indicators used with the compositions and methods described herein are used to detect changes in pH. In certain embodiments, the indicators are used to detect acidity, to prevent hydrolytic degradation of APIs mixed with the indicator by hydrolysis. In certain embodiments, the indicator shows a change in pH when it passes below 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3 4.2, 4.1 or 4.0. In other embodiments, the indicators are used to detect the presence of basic conditions. In certain embodiments, the indicator shows a change in pH when it passes above 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0. In certain embodiments, indicators transition from their home configuration to a first threshold configuration when pH changes to be outside of a certain pH range. These ranges include pH of 6.0-8.0, 6.5-7.5, 5.0-7.0, 7.0-8.0, 7.2-7.6, or 7.0-9.0. In certain embodiments, whether the pH became higher or lower than the desired range, the indicator would transition to its first threshold configuration. According to other embodiments, the indicator could transition to a first threshold configuration if the indicator were exposed to an environment with a pH lower than a desired range and transition to a second threshold configuration if the indicator were exposed to an environment with a pH higher than a desired range. The first and second threshold configurations could be represented by different colors to be differentiated.

According to other embodiments, the indicators used with the compositions and methods described herein are used to detect changes in temperature. In certain embodiments, the indicators are used to detect exposure to high temperatures. Certain APIs become less effective when exposed to high temperatures. In certain embodiments, the indicator shows a change in temperature when it passes above 30, 35, 40, 45, 50, 55, 60, 65, 70, 75, 80, 85, 90, 95, 100, 105, 110, 115 or 120° C. This temperature could be achieved when the indicator is added to a food, beverage or cosmetic that is subject to heating. In other embodiments, the indicators are used to detect exposure to low temperatures. Certain APIs become less effective when exposed to low temperatures, especially if they are exposed to freeze thaw cycles. In certain embodiments, the indicator shows a change in color when it passes below 20, 15, 10, 5, 0, −5, −10, −15, −20, −25, −30, −35 or −40° C. In certain embodiments, indicators transition from their home configuration to a first threshold configuration when exposed to temperature outside of a certain range. These ranges include 10-25, 25-50, −5-5, 0-5, −5-0, 25-50, 90-110° C. In certain embodiments, whether the temperature was higher or lower than the desired range, the indicator would transition to its first threshold configuration. According to other embodiments, the indicator could transition to a first threshold configuration if the indicator were exposed to an environment with a temperature lower than a desired range and transition to a second threshold configuration if the indicator were exposed to an environment with a temperature higher than a desired range. The first and second threshold configurations could be represented by different colors to be differentiated.

In other embodiments, the indicator is able to detect exposure to freezing and/or thawing. In certain embodiments, an indicator can detect the temperature change that accompanies a freeze thaw cycle. In some embodiments, when the indicator has been exposed to a freeze thaw cycle, a first threshold is reached and the color of the indicator changes. In certain embodiments, if the indicator is then exposed to higher or lower changes, it retains the color associated with the first transition configuration triggered by the freeze/thaw event. In other embodiments, the indicator reaches a second, third or additional thresholds with subsequent freeze/thaw events. Thus, the indicator can show a different color depending on the number of freeze/thaw events it is exposed to. In certain embodiments, the indicator need only be exposed to freezing temperatures to show a freeze/thaw event. In other embodiments, the indicator must be exposed to freezing temperatures and then temperatures above freezing to register a freeze/thaw event. Different aqueous and organic solutions have different freezing temperatures. In some embodiments, the freeze/thaw indicator is sensitive to freezing at 0° C. In other embodiments, the freezing temperature is selected from −10, −9, −8, −7, −6, −5, −4, −3, −2, −1, 1, 2, 3, 4, 5, 6, 7, 8, 9 or 10° C.

Indicators can be associated with beads. According to embodiments in which the indicators are administered with an API, the API and indicators can be associated with the same beads or they can be associated with different beads. According to some embodiments, when the APIs and indicators are associated with different beads the beads can be of the same type or different types.

In certain embodiments, beads associated with indicators can be between 300 and 1000 µM in diameter. In other embodiments, the beads associated with indicators can be 300-500, 500-750 or 750-1000 µM in diameter. These larger beads are particularly useful for indicators that show the identity of an API that they are associated with. The greater size of the beads allows the signal (e.g. color) from the indicators to be more easily perceived. These larger sized beads can enhance the signal produced by any type of indicator.

In certain embodiments, the compositions described herein contain only bead associated indicators. These bead associated indicators can then be later mixed with an API to show its identity or used in situations where changes in the values of particular parameters are necessary. Examples of these parameters are provided above.

IV. Kits

The disclosure also provides kits consistent with administration of the compositions described herein. These kits include APIs associated with beads that are coded by indicators. In certain embodiments, the indicators encode the associated beads by color. The color provided by the indicator can be used to color code the pharmaceutical associated with that indicator for ease of selecting and administering pharmaceuticals to a patient population and also providing a quality assurance step by allowing identification of the beads drug product in food or other administration matrices and allowing differentiation from admixed crushed solid oral drug products.

In certain embodiments, each container contains a single dose of API. These doses can be associated with beads and/or indicators. The indicators can also be associated with beads of the same or different type from the API associated beads.

In certain embodiments each container contains a single dose of multiple APIs. These doses can be associated with beads and/or indicators. The indicators can also be associated with beads of the same or different type from the API associated beads.

In certain embodiments, each API is associated with one type of bead. In other embodiments each API is associated with multiple types of beads. These various API associated beads can be mixed to provide various API dosing regimens including time release or various dose amounts. Kits can also include indicators independent of an API. These indicators can be associated with beads of their own or free in solution or suspension. These indicators can be mixed with APIs and potentially the APIs associated beads for any of the detecting needs described above. Thus, an API that needs to have an indicator for pH can be mixed with that appropriate indicator in that situation. APIs will need different indicators depending on the specific API and the mode of administration. The necessary indicator may also be dependent upon the specific food, beverage or cosmetic that the API is being administered in.

In another embodiment, the kits make up a system in which several APIs are associated with beads in separate containers. In some embodiments, each container contains one API. Each API can be associated with beads. In certain embodiments, each of the APIs is associated with an indicator that shows a different color for ease of identification. These APIs could also be associated with specific indicators for detection of any of the properties shown above. In certain embodiments, the system also includes indicators in separate containers such that one container may contain one population of indicators for one environmental parameter, or combinations of two or more indicators to detect two or more parameters. In some embodiments, each container contains one indicator. Each indicator is capable of detecting a different parameter. The system can be used to provide different combinations of APIs associated with beads with different indicators. In certain embodiments, the indicators are also associated with beads independent of the beads that the APIs are associated with. Each API and/or indicator can be associated with differing or similar beads depending on the specific API or indicator.

In certain embodiments, the containers for the APIs or indicators described herein are transparent to reveal the color of the APIs or indicators or the APIs mixed with indicator. In other embodiments, the containers, themselves, are color coded for easy identification of APIs or combinations of APIs and indicators or indicators. The containers can also include identifying marks for quality control purposes. For instance, identifying marks include labels, bar codes or RFID tags. The identifying marks can be readily integrated into the systems already used in medical care facilities. These medical care facilities can be hospitals, hospices, clinics or elder care facilities.

V. Food, Beverage or Cosmetic

According to certain embodiments, the bead associated APIs and in some embodiments, indicators, are sprinkled on or mixed with food, beverage or cosmetics. In certain embodiments, food, beverage and cosmetics are used that fit the temperature and pH limitations of the APIs that are added to them. For instance, some APIs are heat or pH sensitive and lose efficacy if exposed to extremes in temperature or pH. In some embodiments, the food, beverage or cosmetic is heat treated either prior to mixing with the API, during mixing with the API or after mixing with the API.

Foods that can be mixed with the bead associated APIs described herein include soups, cereals, breads, pretzels, chips, popcorn, cooked and or pureed vegetables, corn, carrots, cabbage, lettuce, tomatoes, potatoes, greens, broccoli, cucumbers, celery, mushrooms, radishes, nuts, peanuts, walnuts, pecans, almonds, cashews, cheese, cheddar cheese, Swiss cheese, brie, blue cheese, meats, pastas, fish, white sauce, meat sauce, demi-glace sauce, tomato sauce, curry, stew, cream soup, minestrone, Worcestershire sauce, middle-thick sauce, thick sauce, pork cutlet sauce, seasoning soy sauces, Chinese noodles, buckwheat noodles, jams, jellies, preserves, nut butters, (e.g. peanut, almond, Nutella) yogurt plain or flavored, puddings, white wheat noodles, chops, rice, dumplings, dressings, dried seasoning powder, dipping sauces, frozen foods, ready-to-eat foods, instant foods, beef, chicken, lamb, pork, and others. Beverages include, water, tea, coffee, soda, soda water, tonic water, juice, alcoholic beverages, beer, wine, spirits, milk, pedialyte, electrolyte replenishment drinks and others. Cosmetics include shaving cream, chewing gum, toothpaste, eye drops, make-up, sun block, skin lotion, mouthwash, mints, aftershave lotion, soap, shampoo, conditioner and others.

In certain embodiments, the bead compositions described herein would not substantially change the taste or flavor of the food, beverage or cosmetic it is administered with. In other embodiments, the bead compositions described herein would not substantially change the texture of the food, beverage or cosmetic it is administered with. In other embodiments, the bead compositions described herein would not substantially change the appearance of the food, beverage or cosmetic it is administered with. In other embodiments, the bead compositions described herein would not substantially change the color of the food, beverage or cosmetic it is administered with unless a threshold was reached on a parameter of an indicator included with the beads.

In certain embodiments, APIs cannot be mixed with hot, cold, frozen, acidic or basic foods.

VI. Methods of Administration

The compositions described herein are administered through adding and mixing the bead-associated API with food, beverage and/or cosmetics. In certain embodiments, the compositions described herein are administered through adding and mixing the bead-associated API with food or beverage. In certain embodiments, the compositions described herein are administered through adding and mixing the bead-associated API with food. The bead-associated API can also be associated with an indicator. The indicator can also be associated with its own population of beads such that this population of beads contains an indicator or indicators or other ingredients to otherwise inform potential product safety issues, efficacy issues and quality assurance, but that contains no API (i.e. this is a placebo population of indicator beads). This population of indicator placebo beads may be administered separately from the API-containing beads, such as with other medicinal products, that may be administered and mixed with API-containing beads either as a combined drug product or separately.

According to certain embodiments, each API is associated with beads and one or more indicators in one container. In this embodiment, specific indicators that show the identity, integrity and/or efficacy of the API are present with the API in one pre-made dosage form. In other embodiments, the API is associated with beads, but the indicators are added to the bead-associated API later. The indicators can be added by a health care professional or someone else in the supply chain for the bead associated API. Indicators can be added to the bead associated API depending on the context in which it will be administered. These contexts could vary depending on the specific food, beverage or cosmetic the bead associated API is administered with, the types of drugs the intended patient population tends to be taking or the conditions the bead associated API may experience during transport and storage. The indicators to be added to the bead associated APIs may themselves be associated with their own beads. These indicators may be presented in color coded or transparent containers. The containers and/or the beads themselves may be color coded for easy identification of the indicators. Any of the indicators described above may be used according to these embodiments.

The bead associated APIs may be sprinkled into food, beverage or cosmetics. The bead associated APIs can be mixed with the food, beverage or cosmetics according to any method known in the art.

VII. Pharmaceutical Compositions

In certain embodiments, the APIs described herein are further formulated with a pharmaceutically acceptable carrier. In preferred embodiments, pharmaceutical compositions and formulations described herein are administered orally, transmucosally or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The APIs described herein can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Pharmaceutical formulations of the invention can be prepared according to any method known to the art for the manufacture of pharmaceuticals. Such drugs can contain sweetening agents, flavoring agents, coloring agents and preserving agents. A formulation can be administered with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Aqueous suspensions can contain an active agent in admixture with excipients suitable for the manufacture of aqueous suspensions for mixing with beads. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In certain embodiments, oil-based pharmaceuticals are used for mixing APIs with beads. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

In certain embodiments, the APIs are mixed with beads in oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

In certain embodiments, the pharmaceutical compositions and formulations are delivered transdermally, by a topical route, formulated as applicator sticks, solutions, suspensions, emulsions, gels, creams, ointments, pastes, jellies, paints, powders, and aerosols.

In certain embodiments, the pharmaceutical compositions and formulations are delivered as beads for slow release in the body. For example, beads can be administered via intradermal injection of drug which slowly release after administration, or beads can be administered orally which slowly release in the gut after ingestion see, e.g., Eyles (1997) J. Pharm. Pharmacol. 49:669-674.

In certain embodiments, sustained-release polymers for use in the beads described herein include alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred waxes include for example natural and synthetic waxes, fatty acids, fatty alcohols, and mixtures of the same (e.g., beeswax, carnauba wax, stearic acid and stearyl alcohol). Certain embodiments utilize mixtures of any of the foregoing sustained release materials in the matrix of the core. However, any pharmaceutically acceptable hydrophobic or hydrophilic sustained-release material that is capable of imparting sustained-release of the active agent may be used in accordance with the beads described herein.

In certain embodiments, suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT®. (Degussa AG, Dusseldorf, Germany), including EUDRAGIT® L30D-55 and L100-55 (soluble at pH 5.5 and above), EUDRAGIT® L-100 (soluble at pH 6.0 and above), EUDRAGIT® (soluble at pH 7.0 and above, as a result of a higher degree of esterification), EUDRAGITs® NE, RL and RS (water-insoluble polymers having different degrees of permeability and expandability) and EUDRAGIT® FS3OD a tercopolymer of methacrylic acid, methyl acrylate and methylmethacrylate; vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multi-layer coatings using different polymers can also be applied. The preferred coating weights for particular coating materials can be readily determined by those skilled in the art by evaluating individual release profiles for tablets, beads and granules prepared with different quantities of various coating materials. It is the combination of materials, method and form of application that produce the desired release characteristics, which can be determined by those of skill in the art, considering the nature of the compound to be adsorbed, as well as other relevant factors.

In other embodiments, the coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84: 1 144-1 146; Rohatagi (1995) Pharmazie 50:610-613; Brophy (1983) Eur. J. Clin. Pharmacol. 24: 103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regimen, i.e., dose schedule and dosage levels, administered practicing the methods of the invention are correct and appropriate. Single or multiple administrations of formulations can be given depending on for example: the dosage and frequency as required and tolerated by the patient, the degree and amount of cholesterol homeostasis generated after each administration, and the like. The formulations should provide a sufficient quantity of active agent to effectively treat, prevent or ameliorate conditions, diseases or symptoms, e.g., treat obesity.

In certain embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington: The Science and Practice of Pharmacy, 21st ed., 2005.

EXAMPLES

The present invention is further illustrated by the following examples, which should not be construed as further limiting. The contents of and all references, patents and published patent applications cited throughout this application are expressly incorporated herein by reference.

Example 1

Bead Drug Product

A composition (of one of a series) of bead drug product is described herein. The generic medicinal chemical Metoprolol succinate (indicated for the treatment of hypertension) as well as a population of placebo-containing indicator beads (capable of indicating the potential for product degradation due to environmental factors or compromise of drug release characteristics) are combined. This drug product can be used as a system to facilitate drug oral delivery to hypertensive patients with dysphagia, using beads designed for administration in foodstuffs. The drug product helps alleviate pain and other difficulties associated with swallowing solid oral medicinal products experienced by patients with dysphagia.

Current Approach

Metoprolol succinate is formulated as a solid oral dosage form (tablet). The Metoprolol succinate tablets are ingested whole, with accompanying symptoms of dysphagia, once daily (long acting once daily formulation; this formulation cannot be crushed under any circumstances). Alternatively the tablets are given twice daily (immediate release formulation) and are crushed manually or using a device and admixed with foodstuffs, exposing the active pharmaceutical ingredients to food contents. Crushing tablets adulterates the pharmacology and compromises dosing accuracy introducing toxicity and efficacy issues for patients and safety issues for drug administration staff.

Bead Based Approach

In one embodiment, Metoprolol succinate active pharmaceutical ingredient is made into drug product beads by rotogranulation. In one embodiment the beads are round in shape and 300 microns in diameter on average. In one embodiment the drug substance beads are coated with ethylcellulose in order to regulate dissolution rate and in order to protect the drug from exposure to food. The dissolution rate and other physical and chemical parameters of the drug substance beads are based on the existing data for the reference product that will be used to establish bioequivalence consistent with regulatory requirements. In one embodiment the drug substance beads are coated with a white coating. In one embodiment the white coating is overlaid with a blue coating to uniquely identify the API contained therein, and that blue coating will dissolve after a period of time to reveal the white color underneath. The appearance of white color indicates that the protective coating(s) on the beads have been dissolved and that the API is in imminent danger of being exposed to foodstuffs and other drugs mixed in the foodstuffs (i.e. signals the potential of drug product compromise). In one embodiment the beads have a clear coat as the most external layer. In another embodiment the finished drug product beads have a diameter of 240 microns on average. In another embodiment the finished drug product beads provide a single daily dose consistent with the reference product and regulatory requirements. Appropriate testing will establish dissolution rate and other pharmacological parameters, bio-equivalence, and food compatibility.

In other embodiments, a population of indicator beads is added to the drug product beads to comprise the final drug product. In one embodiment the indicator beads are placebo (i.e. they contain no active pharmaceutical ingredient). In another embodiment, the indicator beads are added at a ratio of approximately 10:1 (active drug product:placebo indicator). In another embodiment, the indicator beads are approximately round in shape and approximately 200 microns in diameter on average. In another embodiment, the indicator beads are composed of sub-populations of some indicator beads for environmental temperature and some indicator beads for environmental acidity. The indicators allow detection of potential product compromise or degradation in foodstuffs. In another embodiment, all of the indicator beads are blue in color. In another embodiment, the temperature indicator beads (sub-population of indicator beads) turn from blue to white and stay white if there has been an excursion beyond the tested product stability upper limit of 37 degrees Celsius. In another embodiment, the freeze/thaw indicator beads turn from blue to white and stay white if the beads have been exposed to temperatures lower than 0 degrees Celsius and subsequently warmed. In another embodiment, the pH indicator beads turn from blue to white and stay white if the beads have been exposed to pH>6.

In further embodiments, the final drug product, designed and formulated for safety and efficacy in food, contains a population of beads that is comprised of a once daily administration population of round Metoprolol succinate containing beads, blue in color (soluble blue layer), averaging 240 microns in diameter, with white undercoating (to indicate solubilization when exposed). The final drug product is also comprised of a population of placebo indicator beads, blue in color, round and approximately 100 microns in diameter on average, at a ratio of approximately 1:10 (indicator:active) which is in turn comprised of sub-populations of indicators that turn white when exposed to pH>6, temperatures below 0 degrees Celsius, and temperatures above 37 degrees Celsius.

Example 2

Bead Drug Product

A composition (of one of a series) of bead drug product is described herein. The generic medicinal chemical Nifedipine (indicated for the treatment of hypertension and angina) as well as a population of placebo-containing indicator beads (capable of indicating the potential for product degradation due to environmental factors or compromise of drug release characteristics) are combined. This drug product can be used as a system to facilitate drug oral delivery to hypertension or angina patients with dysphagia, using beads designed for administration in foodstuffs. The drug product helps alleviate pain and other difficulties associated with swallowing solid oral medicinal products experienced by patients with dysphagia.

Current Approach

Nifedipine is formulated as a solid oral dosage form (tablet), both long acting (once daily) or immediate release forms (three times daily). The Nifedipine tablets are ingested whole, with accompanying symptoms of dysphagia, once daily (long acting once daily formulation; this formulation cannot be crushed under any circumstances) Immediate release tablets are not recommended for administration to the elderly according to the Beers List, a recognized published listing of medications that may be dangerous and/or inappropriate in the elderly. The only approved option for Nifedipine patients, therefore, is to ingest whole once daily tablets.

Bead Based Approach

In one embodiment, Nifedipine active pharmaceutical ingredient is made into drug product beads by hot melt extrusion. In one embodiment the beads are round in shape and 250 microns in diameter on average. In one embodiment the drug substance beads are coated with wax layers in order to regulate dissolution rate and in order to protect the drug from exposure to food. The dissolution rate and other physical and chemical parameters of the drug substance beads are based on the existing data for the reference product that will be used to establish bio-equivalence consistent with regulatory requirements. In one embodiment the drug substance beads are coated with a white coating. In one embodiment the white coating is overlaid with a red coating to uniquely identify the API contained therein. The red coating is comprised of red color and polymers that degrade when exposed to pH<4. The appearance of white color indicates that the API is in imminent danger of being exposed to an acidic environment (i.e.). In one embodiment the beads have a clear coat as the most external layer. In another embodiment the finished drug product beads have a diameter of 280 microns on average. In another embodiment the finished drug product beads provide a single daily dose consistent with the reference product and regulatory requirements. Appropriate testing will establish dissolution rate and other pharmacological parameters, bio-equivalence, and food compatibility.

In further embodiments, the final drug product, designed and formulated for safety and efficacy in food, contains a population of beads that is comprised of a once daily administration population of round Nifedipine-containing beads, red in color, wherein the red color layer is comprised of red color and a pH-sensitive polymer. In certain aspects the red layer is such that it will dissolve when exposed to pH<4 exposing the white layer underneath, indicating the API is in imminent danger of being exposed to an acidic environment and signaling the potential of drug product compromise.

Example 3

Bead Drug Product

A composition (of one of a series) of bead drug product is described herein. The generic medicinal chemical Isosorbide mononitrate (indicated for the treatment of angina) as well as a population of placebo-containing indicator beads (capable of indicating the potential for product degradation due to environmental factors or compromise of drug release characteristics) are combined. This drug product can be used as a system to facilitate drug oral delivery to hypertensive patients with dysphagia, using beads designed for administration in foodstuffs. The drug product helps alleviate pain and other difficulties associated with swallowing solid oral medicinal products experienced by patients with dysphagia.

Current Approach

Isosorbide mononitrate is formulated as a solid oral dosage form (tablet). The isosorbide mononitrate tablets are ingested whole, with accompanying symptoms of dysphagia, once daily (long acting once daily formulation; this formulation cannot be crushed under any circumstances). Alternatively the tablets are given twice daily (immediate release formulation; this formulation cannot be crushed under any circumstances) and are ingested whole, with accompanying symptoms of dysphagia. Crushing any solid oral formulation of Isosorbide mononitrate is contraindicated.

Bead Based Approach

In one embodiment, active pharmaceutical ingredient is made into drug product beads by extrusion and spheronization. In one embodiment the beads are round in shape and 250 microns in diameter on average. The dissolution rate and other physical and chemical parameters of the drug substance beads are based on the existing data for the reference product that will be used to establish bio-equivalence consistent with regulatory requirements. In one embodiment the drug substance beads are coated with a white coating. In one embodiment the white coating is overlaid with a yellow coating to uniquely identify the API contained therein, and that yellow coating will dissolve after a period of time to reveal the white color underneath. The appearance of white color indicates that the protective coating(s) on the beads have been dissolved and that the API is in imminent danger of being exposed to foodstuffs and other drugs mixed in the foodstuffs (i.e. signals the potential of drug product compromise). In one embodiment the beads have a clear coat as the most external layer. In another embodiment the finished drug product beads have a diameter of 280 microns on average. In another embodiment the finished drug product beads provide a single daily dose consistent with the reference product and regulatory requirements. Appropriate testing will establish dissolution rate and other pharmacological parameters, bio-equivalence, and food compatibility.

In other embodiments, a population of indicator beads is added to the drug product beads to comprise the final drug product. In one embodiment the indicator beads are placebo (i.e. they contain no active pharmaceutical ingredient). In another embodiment, the indicator beads are added at a ratio of approximately 15:1 (active drug product:placebo indicator). In another embodiment, the indicator beads are approximately round in shape and approximately 250 microns in diameter on average. In another embodiment, the indicator beads are composed of sub-populations of indicator beads for environmental temperature. The indicators allow detection of potential product compromise or degradation in foodstuffs. In another embodiment, all of the indicator beads are yellow in color. In another embodiment, the indicator beads are comprised of two sub-populations of beads. In one aspect of this embodiment, one sub-population of indicator beads has a yellow outer layer comprised of yellow color and polymers that degrade above 30 degrees Celsius. In another aspect of this embodiment the yellow indicator layer overlays a white layer such that when the yellow layer is exposed to high temperature and degrades, then the white layer is exposed. This indicates a critical temperature excursion and signals the potential of drug product compromise. In another aspect of this embodiment, one sub-population of indicator beads has a yellow outer layer comprised of yellow color and polymers that fracture below 0 degrees Celsius. In another aspect of this embodiment the yellow indicator layer overlays a white layer such that when the yellow layer is exposed to freezing and thawing it degrades, and the white layer is exposed.

In further embodiments, the final drug product, designed and formulated for safety and efficacy in food, contains a population of beads that is comprised of a once daily administration population of round Isosorbide mononitrate-containing beads, yellow in color (soluble yellow layer), averaging 280 microns in diameter, with white undercoating (to indicate solubilization when exposed). The final drug product is also comprised of a population of placebo indicator beads, yellow in color, round and approximately 250 microns in diameter on average, at a ratio of approximately 1:15 (indicator:active) which is in turn comprised of two sub-populations of indicators that turn white when exposed to freeze/thaw conditions or temperatures above 30 degrees Celsius.

Example 4

Bead Indicator Product (Medicinal Use)

A composition (of one of a series) of bead indicator product for medicinal use is described herein. The indicator beads are intended to mix with other forms of powdered or beaded drugs that will be administered to patients admixed with foodstuffs. The bead indicator contains no active medicinal ingredient and allows for detection of environmental conditions that could degrade or compromise the drug products being administered, such as freeze/thaw, high temperature and high or low pH.

Current Drug Administration in Elderly

Drugs are often administered to the elderly in foodstuffs. Most drugs are crushed, added to food and then administered.

Drug Administration Using Indicator Beads

In certain embodiments, indicator beads are added to the drug product before or during mixing with food. In certain embodiments the indicator beads are added at the time of primary packaging. In other embodiments the indicator beads are added at the time of drug administration when the drugs and indicator beads are mixed together in food. In one embodiment, the indicator beads are added at a ratio of approximately 10:1 (active drug product:placebo indicator). In another embodiment, the indicator beads are approximately round in shape and approximately 250 microns in diameter on average. In another embodiment, the indicator beads are composed of sub-populations of indicator beads for environmental temperature and pH. The indicators allow detection of potential product compromise or degradation in foodstuffs. In another embodiment, all of the indicator beads are red in color. In another embodiment, the indicator beads are comprised of three sub-populations of beads. In one aspect of this embodiment, one sub-population of indicator beads has a red outer layer comprised of red color and polymers that degrade above 30 degrees Celsius. In another aspect of this embodiment the red indicator layer overlays a white layer such that when the red layer is exposed to high temperature and degrades, then the white layer is exposed. This indicates a critical temperature excursion and signals the potential of drug product compromise. In another aspect of this embodiment, one sub-population of indicator beads has a red outer layer comprised of red color and polymers that fracture below 0 degrees Celsius. In another aspect of this embodiment the red indicator layer overlays a white layer such that when the red layer is exposed to freezing and thawing it degrades, and the white layer is exposed. In another aspect of this embodiment, one sub-population of indicator beads has a red outer layer comprised of red color and polymers that degrade below pH 4. In another aspect of this embodiment the red indicator layer overlays a white layer such that when the red layer is exposed to low pH it degrades, and the white layer is exposed.

Example 5

Bead Indicator Product (Food Industry Use)

A composition (of one of a series) of bead indicator product for use in the quality assurance of food is described herein. The indicator beads are intended to mix with foodstuffs. The bead indicator contains no active medicinal ingredient and allows for detection of environmental conditions that could degrade or compromise or result from the degradation or compromise of the food, such as freeze/thaw, high temperature and high or low pH.

Quality Assurance of Foodstuffs Using Indicator Beads

In certain embodiments, indicator beads are added to the food product. In certain embodiments the indicator beads are added at the time of primary packaging. In other embodiments the indicator beads are added at some point during manufacture. In other embodiments indicator beads are added by the consumer. In one embodiment, the indicator beads are approximately round in shape and approximately 350 microns in diameter on average. In another embodiment, the indicator beads are composed of sub-populations of indicator beads for environmental temperature and pH. The indicators allow detection of potential product compromise or degradation in foodstuffs. In another embodiment, all of the indicator beads are blue in color. In another embodiment, the indicator beads are comprised of three sub-populations of beads. In one aspect of this embodiment, one sub-population of indicator beads has a blue outer layer comprised of blue color and polymers that degrade above 30 degrees Celsius. In another aspect of this embodiment the blue indicator layer overlays a white layer such that when the blue layer is exposed to high temperature and degrades, then the white layer is exposed. This indicates a critical temperature excursion and signals the potential of drug product compromise. In another aspect of this embodiment, one sub-population of indicator beads has a blue outer layer comprised of blue color and polymers that fracture below 0 degrees Celsius. In another aspect of this embodiment the blue indicator layer overlays a white layer such that when the blue layer is exposed to freezing and thawing it degrades, and the white layer is exposed. In another aspect of this embodiment, one sub-population of indicator beads has a blue outer layer comprised of blue color and polymers that degrade above pH 7. In another aspect of this embodiment the blue indicator layer overlays a white layer such that when the blue layer is exposed to high pH it degrades, and the white layer is exposed.

What is claimed is:

1. A composition comprising an active pharmaceutical ingredient formulated into a first group of beads between 50 and 1000 μm in diameter, and a second group of beads comprising one or more indicators, wherein the one or more indicators provide information regarding pH, temperature changes or the occurrence of freeze-thaw.

2. The composition of claim 1, wherein the one or more indicators provide information regarding lowering of pH below 8.

3. The composition of claim 1, wherein the one or more indicators provide information regarding raising pH above 6.

4. The composition of claim 1, wherein the temperature change comprises a drop in temperature below 10° C.

5. The composition of claim 1, wherein the temperature change comprises a rise in temperature above 30° C.

6. The composition of claim 1, wherein the one or more indicators changes color in order to provide information, wherein the color change is optionally from white or gray to red, green, blue, orange, yellow or violet.

7. The composition of claim 6, wherein at least one of the one or more indicators is selected from the group consisting of Reflex Blue, Black Pantone 7C 2x, Red 192, Process Magenta, Orange 165, Green 349, green C, Purple 2735, Yellow 100U, gentian violet, leucomalachite green, thymol blue, methyl yellow, bromophenol blue, congo red, methyl orange, screened methyl orange, bromocresol green, methyl red, azolitmin, bromocresol purple, bromothymol blue, phenol red, neutral red, naphtholphthalein, cresol red, phenolphthalein, thymolphthalein, and alizarene yellow R.

8. The composition of claim 1, wherein the one or more indicators comprise a coloured layer that is exposed when an outer layer or layers is changed by the environmental conditions.

9. The composition of claim 1, wherein the beads in the second set of beads are coated with a polymeric chemical, said polymeric chemical
   a. degrades above a certain temperature, exposing a coloured indicator layer underneath;
   b. fractures at or below 0 degrees Celsius revealing a coloured indicator layer underneath;
   c. degrades when exposed to low pH, revealing a coloured indicator layer underneath; or
   d. degrades when exposed to high pH, revealing a coloured indicator layer underneath.

10. The composition of claim 1 wherein
the beads of the first group are between 50 and 300 μm in diameter and
the beads of the second group are between 50 and 1000 μm in diameter.

11. The composition of claim 1, wherein the one or more indicators provide information regarding lowering of pH below 7.5.

12. The composition of claim 1, wherein the one or more indicators provide information regarding lowering of pH below 7.0.

13. The composition of claim 1, wherein the one or more indicators provide information regarding lowering of pH below 6.5.

14. The composition of claim 1, wherein the one or more indicators provide information regarding raising pH above 6.

15. The composition of claim 1, wherein the one or more indicators provide information regarding raising pH above 6.5.

16. The composition of claim 1, wherein the one or more indicators provide information regarding raising pH above 7.0.

17. The composition of claim 1, wherein the one or more indicators provide information regarding raising pH above 7.5.

18. The composition of claim 1, wherein the temperature change comprises a drop in temperature below 5° C.

19. The composition of claim 1, wherein the temperature change comprises a rise in temperature above 50° C.

* * * * *